United States Patent
De Vos

(10) Patent No.: US 10,857,189 B2
(45) Date of Patent: Dec. 8, 2020

(54) COMPOSITIONS AND METHODS FOR PREVENTING AND/OR TREATING VITAMIN B12 DEFICIENCY

(71) Applicant: Caelus Pharmaceuticals B.V., Zegveld (NL)

(72) Inventor: Willem Meindert De Vos, Ede (NL)

(73) Assignee: Caelus Pharmaceuticals B.V., Zegveld (NL)

( * ) Notice: Subject to any disclaimer, the term of this patent is extended or adjusted under 35 U.S.C. 154(b) by 188 days.

(21) Appl. No.: 16/075,073

(22) PCT Filed: Feb. 27, 2017

(86) PCT No.: PCT/NL2017/050119
§ 371 (c)(1),
(2) Date: Aug. 2, 2018

(87) PCT Pub. No.: WO2017/146580
PCT Pub. Date: Aug. 31, 2017

(65) Prior Publication Data
US 2019/0038678 A1 Feb. 7, 2019

(30) Foreign Application Priority Data
Feb. 25, 2016 (NL) ..................................... 2016323

(51) Int. Cl.
| A61K 35/74 | (2015.01) |
| A61P 1/14 | (2006.01) |
| A61P 1/18 | (2006.01) |
| A61P 3/04 | (2006.01) |
| A61P 31/18 | (2006.01) |
| A61K 9/19 | (2006.01) |
| A61K 9/20 | (2006.01) |
| A61K 47/02 | (2006.01) |

(52) U.S. Cl.
CPC .............. *A61K 35/74* (2013.01); *A61K 9/19* (2013.01); *A61K 9/2081* (2013.01); *A61K 47/02* (2013.01); *A61P 1/14* (2018.01); *A61P 1/18* (2018.01); *A61P 3/04* (2018.01); *A61P 31/18* (2018.01)

(58) Field of Classification Search
CPC ........................................................ A61P 3/04
See application file for complete search history.

(56) References Cited

U.S. PATENT DOCUMENTS

| 9,433,650 B2 | 9/2016 | Nieuwdorp et al. | |
| 9,623,055 B2 | 4/2017 | Nieuwdorp et al. | |
| 2007/0258953 A1* | 11/2007 | Duncan | A23C 9/12 424/93.4 |
| 2014/0242624 A1 | 8/2014 | Levinson | |

FOREIGN PATENT DOCUMENTS

| WO | 2013032328 A1 | 3/2013 |
| WO | 2014150094 A1 | 9/2014 |
| WO | 2016110585 A1 | 7/2016 |
| WO | 2017116235 A1 | 7/2017 |
| WO | 2017146580 A1 | 8/2017 |

OTHER PUBLICATIONS

Udayappan et al., Ned. Tijdschr. Diabet. 11, 145 (2013). PS4—5, 1 page.*
Russian Office Action for Russian Application No. 2018133333/10, dated Nov. 18, 2019, 12 pages (with English Translation).
Sahibgaraeva et al. "Characterization of B12 vitamins and main producers upon receipt thereof" Pharmaceutical technology and nanotechnology. Development and registration of medicines., 2015, N 3 (12), pp. 104-106. (Eng. Abstract).
Santos et al., "Effect of Amino Acid Availability on Vitamin B12 Production in Lactobacillus reuteri" Applied and Environmental Microbiology, Jun. 2009, p. 3930-3936 vol. 75, No. 12.
Collado et al."Intestinal Integrity and Akkermansia muciniphila, a Mucin-Degrading Member of the Intestinal Microbiota Present in Infants,Adults, and the Elderly" Applied and Environmental Microbiology, Dec. 2007, p. 7767-7770 vol. 73, No. 23, American Society for Microbiology.
Molina et al., Lactobacillus reuteri CRL 1098 prevents side effects produced by a nutritional vitamin B12 deficiency, Journal of Applied Microbiology, Feb. 1, 2009, pp. 467-473, vol. 106, No. 2, Wiley-Blackwell Publishing Ltd, GB.
Klaring et al., Intestinimonas butyriciproducens gen. nov., sp. Nov., a butyrate-producing bacterium from the mouse intestine, International Journal of Systematic and Evolutionary Microbiology, Aug. 5, 2013, pp. 4606-4612, vol. 63, No. Pt 12.
Engels et al., The Common Gut Microbe Eubacterium hallii also Contributes to Intestinal Propionate Formation, Frontiers in Microbiology, May 19, 2016, pp. 1-12, vol. 7.
Santos et al., Pseudovitamin B12 is the corrinoid produced by Lactobacillus reuteri CRL 1098 under anaerobic conditions, FEBS Letters, Oct. 8, 2007, pp. 4865-4870, vol. 581, No. 25, Elsevier Amsterdam, NL.
PCT International Search Report and Written Opinion, PCT/NL2017/050119, dated Jun. 14, 2017.
Search Report and Written Opinion, NL 2016323, date of completion of report was Oct. 27, 2016.
Van Passel et al., The Genome of Akkermansia muciniphila, a Dedicated Intestinal Mucin Degrader, and Its Use in Exploring Intestinal Metagenomes, 2011, PloSOne 6, e16876.
Taga and Walker, Guest Commentary, 2008, J Bacteriol 190(4), 1157-1159.
Smith et al., The microbial metabolites, short chain fatty acids, regulate colonic Treg cell homeostasis, 2013, Science 341(6145), 569-573.

(Continued)

*Primary Examiner* — Bin Shen
(74) *Attorney, Agent, or Firm* — TraskBritt

(57) ABSTRACT

A method for preventing and/or treating vitamin B12 deficiency is taught. The method comprises administering a composition comprising pseudovitamin B12-producing bacteria, optionally in conjunction with mucin-degrading and/or propionate-producing bacteria, to a subject in need thereof. The method is particularly suitable for administration to subjects suffering from vitamin B12 deficiency due to metformin treatment for type-2 diabetes, and to subjects having undergone bariatric surgery.

21 Claims, 1 Drawing Sheet

(56) References Cited

OTHER PUBLICATIONS

Serna-Cock and Vallejo-Castillo, Probiotic encapsulation, 2013, Afr J of Micobiol Res 7(40), 4743-4753.

Reunanen et al., Akkermansia muciniphila Adheres to Enterocytes and Strengthens the Integrity of the Epithelial Cell Layer, 2015, Appl Environ Microbiol 81, 3655-3662.

Le Poul et al., Functional Characterization of Human Receptors for Short Chain Fatty Acids and Their Role in Polymorphonuclear Cell Activation, 2003, J Biol. Chem 278, 25481-25489.

Hosseini et al., Propionate as a health-promoting microbial metabolite in the human gut, 2011, Nutrition Reviews 69, 245-258.

Guarner and Malagelada, Gut flora in health and disease, 2003, The Lancet 361, 512-519.

Everard et al., Cross-talk between Akkermansia muciniphila and intestinal epithelium controls diet-induced obesity, 2013, PNAS 110, 9066-9071.

Erny et al., Host microbiota constantly control maturation and function of microglia in the CNS, 2015, Nat Neurosci 18(7), 965-977.

Doets et al., Systematic Review on Daily Vitamin B12 Losses and Bioavailability for Deriving Recommendations on Vitamin B12 Intake with the Factorial Approach, 2013, Ann Nutr Metab 62, 311-322.

Derrien et al., *Akkermansia muciniphila* gen. nov., sp. nov., a human intestinal mucin-degrading bacterium, 2004, Int J Syst Evol Microbiol 54(5), 1469-1476.

Degnan et al., Vitamin B12 as a modulator of gut microbial ecology, 2014, Cell Metab. 20(5), 769-788.

Chambers et al., Effects of targeted delivery of propionate to the human colon on appetite regulation, body weight maintenance and adiposity in overweight adults, 2015, Gut 64 (11), 1744-1754.

Canfora et al., Short-chain fatty acids in control of body weight and insulin sensitivity, 2015, Nature Reviews Endocrinology 11, 577-591.

Brown et al., The Orphan G Protein-coupled Receptors GPR41 and GPR43 Are Activated by Propionate and Other Short Chain Carboxylic Acids, 2003, J. Biol. Chem 278, 11312-19.

Anderson et al., One Pathway Can Incorporate either Adenine or Dimethylbenzimidazole as an alpha-Axial Ligand of B12 Cofactors in *Salmonella enterica*, 2008, J Bacteriol 190(4), 1160-1171.

\* cited by examiner

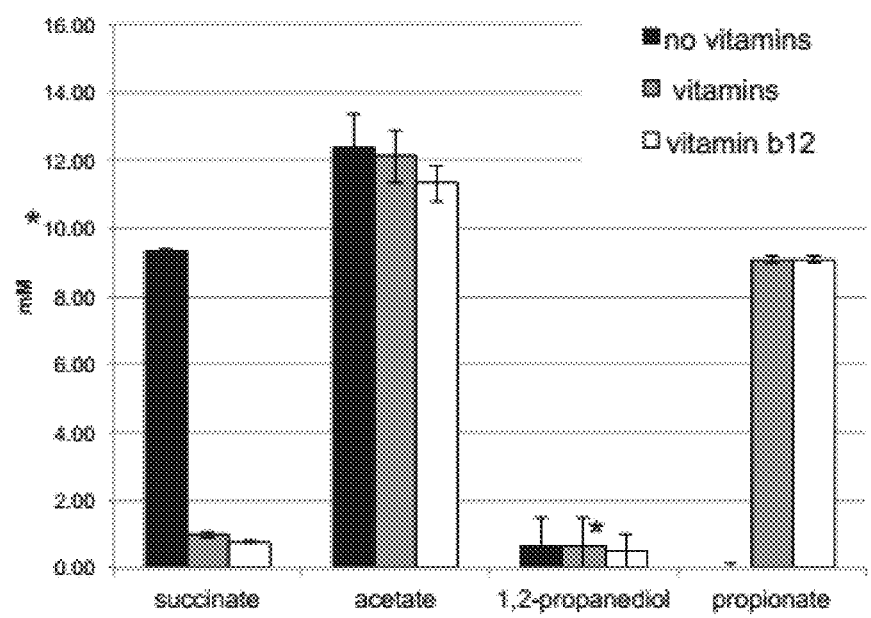

COMPOSITIONS AND METHODS FOR PREVENTING AND/OR TREATING VITAMIN B12 DEFICIENCY

CROSS-REFERENCE TO RELATED APPLICATIONS

This application is a national phase entry under 35 U.S.C. § 371 of International Patent Application PCT/NL2017/050119, filed Feb. 27, 2017, designating the United States of America and published in English as International Patent Publication WO 2017/146580 A1 on Aug. 31, 2017, which claims the benefit under Article 8 of the Patent Cooperation Treaty to The Netherlands Patent Application Serial No. 2016323, filed Feb. 25, 2016.

TECHNICAL FIELD

This application relates to the fields of vitamin B12 production and preventing and/or treating vitamin B12 deficiency, intestinal microbiota, gut mucosal barrier and pharmaceutical, food, or feed or probiotic compositions comprising pseudovitamin B12-producing bacteria *Eubacterium hallii* (*E. hallii*) and/or *Intestinimonas butyriciproducens* (*I. butyriciproducens*) and, optionally, one or more propionate-producing and/or mucin-degrading bacteria, such as *Akkermansia muciniphila* (*A. muciniphila*). Also provided are methods and uses of *E. hallii* and/or *I. butyriciproducens* bacteria, as well as compositions comprising *E. hallii* and/or *I. butyriciproducens*, and, optionally, propionate-producing and/or mucin-degrading bacteria such as *A. muciniphila* for: 1) for preventing and/or treating vitamin B12 deficiency in a subject, 2) for promoting and/or increasing the production of pseudovitamin B12 in the intestine of a subject, and/or 3) for promoting and/or increasing the production of propionate in the intestine of a subject.

BACKGROUND

Corrinoids are cobalt-containing molecules that function as enzyme cofactors in a wide variety of organisms. Specific corrinoids are identified by the structure of their axial ligands. The lower axial ligand of a corrinoid may be a benzimidazole, purine, or phenolic compound. The B12 cofactor most commonly found in animals and many bacteria contain 5,6-dimethylbenzimidazole (DMB) as the axial ligand. This particular B12 cofactor is commonly referred to as vitamin B12.

Only prokaryotes have the enzymes required for the synthesis of corrinoids. Neither fungi, plants, nor animals (including humans) are capable of producing corrinoids such as vitamin B12. Animals and humans rely on food naturally rich in corrinoids such as vitamin B12 (e.g., eggs, fish, meat, and others) or products fortified with corrinoids such as vitamin B12 or vitamin B12 supplements as sources of vitamin B12. Additionally, gut microbiota may provide corrinoids such as vitamin B12 to animals and humans. Vitamin B12 can be produced industrially only through a bacterial fermentation-synthesis.

Vitamin B12, also referred to as cobalamin, is a water-soluble vitamin that is known to play a role in DNA synthesis, optimal hemopoiesis and proper brain development and neurological functions. Vitamin B12 is normally involved in the metabolism of every cell of the human body, especially affecting DNA synthesis and regulation, but also fatty acid metabolism and amino acid metabolism.

B12 cofactors with axial ligands other than DMB are known, with the most common example being pseudovitamin B12, in which N7-linked adenine replaces DMB as the axial ligand.

Over a dozen enzymatic reactions in human and intestinal bacteria have been described to use vitamin B12 as a cofactor. While in humans, these include reactions catalyzed by methylmalonyl-CoA mutase and B12-dependent methionine synthase, in intestinal bacteria, an additional set of vitamin B12-dependent enzymes are present (Degnan et al. 2014, *Cell Metab.* 20(5):769-778). Not all gut bacteria produce vitamin B12. Therefore, some gut bacteria depend on vitamin B12-producing gut bacteria for their vitamin B12 supply. The availability of vitamin B12, therefore, also has an effect on intestinal bacteria and contributes to the structure and function of gut microbial communities. As vitamin B12 can be limiting for humans, it follows that also vitamin B12 limitations exist in the intestinal tract. Vitamin B12 is needed for the full range of microbial conversions in the intestinal tract.

Among these conversions is the production of propionate via the vitamin B12-dependent methylmalonyl-CoA mutase. Propionate and butyrate are among the most important short chain fatty acids (SCFAs) produced in the intestinal tract by fermentation from dietary or host components. These SCFAs have different functions in the human body; where butyrate is mainly fueling the colonocytes, propionate is mainly metabolized in the liver (Guarner and Malagelada, 2003, *The Lancet* 361:512-519). In addition, SCFAs have effects on colon morphology and function as lowering pH, increase in cell proliferation and fecal bulk and modification of the microbial composition. SCFAs also control body weight and insulin sensitivity (Canfora et al., 2015, *Nature Reviews Endocrinology* 11:577-591). Moreover, SCFAs have been found to signal to the host via G-protein-coupled receptors (GPR41 and GPR43) that have been shown to affect the immune system among others via regulatory T cells in mice (Brown et al., 2003, *J. Biol. Chem.* 278:11312-11319; Le Poul et al., 2003, *J. Biol. Chem.* 278:25481-25489; Smith et al., 2013, *Science* 341(6145):569-573). Finally, SCFAs also signal to the neuronal circuits via the FFAR2 receptor (Erny et al., 2015, *Nat. Neurosci.* 18(7):965-977). Propionate is a substrate for hepatic gluconeogenesis and has inhibitory effects on lipid and cholesterol synthesis and protective effects on inflammation and carcinogenesis (Hosseini et al., 2011, *Nutrition Reviews* 69:245-258). Dietary interventions in human have shown that propionate also has been found to increase satiety and regulate appetite, resulting in body weight maintenance in overweight adults (Chambers et al., 2015, *Gut* 64(11):1744-1754).

Recommended daily amount (RDA) for vitamin B12 vary with age, gender, and pregnancy status. For instance, RDA for vitamin B12 for an adult is about 2.4 micrograms/day (for both males and females). However, the RDA for vitamin B12 is not always achieved, either due to insufficient intake of vitamin B12 from the diet or other conditions leading to low or insufficient vitamin B12 levels. Insufficient or limited vitamin B12 intake is typically observed in subjects with specific dietary patterns, such as vegetarians and vegans or as a result of diseases or medical conditions including pernicious anemia, atrophic gastritis, chronic inflammation of the pancreas, surgical procedure where part of the stomach and/or small intestine are removed (including weight loss surgery), condition affecting the small intestine (e.g., Crohn's disease, celiac disease, bacterial growth, or a parasite and the like), heavy drinking, immune system disorders (e.g., Graves' disease or lupus), long-term use of acid-reducing drugs, malnutrition, eating disorders (e.g., bulimia or anorexia nervosa), and others.

Other diseases or medical conditions leading to low or insufficient vitamin B12 levels include HIV/AIDS, metformin treatment for type-2 diabetes patients, obesity or high body mass index (BMI), pre-diabetes state or obesity accompanied by pre-diabetic status or insulin resistance, genetic disorders such as hereditary deficiency of transcobalamin I and/or II, and many others.

An individual with low or insufficient vitamin B12 levels, either due to dietary deficiencies or disease status as mentioned above, may be at risk of developing vitamin B12 deficiency. Depending on the severity, duration of vitamin B12 deprivation or limitation and life stage (childhood, adulthood, old age), vitamin B12 deficiency may lead to a spectrum of diseases from asymptomatic to serious hematologic, neurologic and psychiatric manifestations and the possible risk of irreversible neurological damage despite treatment.

A subject suffering from vitamin B12 deficiency may exhibit one or more symptoms such as diarrhea or constipation, fatigue, lack of energy, light-headedness when standing up, loss of appetite, pale skin, problems concentrating, shortness of breath (mostly during exercise), swollen red tongue or bleeding gums, confusion or change in mental status (e.g., dementia), depression, loss of balance, numbness and tingling of hands and feet, and others.

Vitamin B12 deficiency is typically diagnosed in a subject by measuring vitamin B12 levels in the blood. Typically, vitamin B12 blood levels below 120-180 picomole/L (170-250 pg/mL) in adults are indicative of vitamin B12 deficiency. Elevated methylmalonic acid levels in blood (values >0.4 micromole/L) may also indicate vitamin B12 deficiency.

Treatments to remedy or alleviate vitamin B12 deficiency-related conditions in a subject include intake of vitamin B12 supplements or vitamin B12 injection and/or changes in diet (i.e., introducing food rich in vitamin B12). One of the limitations of vitamin B12 supplementation is that the efficacy of such treatment may be limited or unsatisfactory in subjects with compromised ability to absorb vitamin B12 across the gastrointestinal tract, such as a subject treated with metformin or other drugs causing malabsorption of vitamin B12 or low blood levels of vitamin B12.

Therefore, there is a need for compositions and methods for preventing, treating or alleviating and/or improving vitamin B12 deficiency in a subject.

BRIEF SUMMARY

This disclosure relates to a composition comprising *Eubacterium hallii* and/or *Intestinimonas butyriciproducens* and a physiologically acceptable carrier for use in treating and/or preventing vitamin B12 deficiency in a subject.

In an embodiment, the vitamin B12 deficiency in the subject is derived from or caused by metformin treatment for type-2 diabetes, pernicious anemia, atrophic gastritis, chronic inflammation of the pancreas, surgical procedures where part of the stomach and/or small intestine are removed, weight loss (bariatric) surgery, inflammatory bowel disease (such as Crohn's disease, ulcerative colitis, and the like), celiac disease, bacterial growth, heavy drinking, Graves' disease, lupus, long-term use of acid-reducing drugs, malnutrition, bulimia and anorexia nervosa, HIV/AIDS, obesity, high body mass index, pre-diabetes state, insulin resistance, or a vegetarian or vegan diet.

The composition for use taught herein may further comprise a propionate-producing bacterium, such as *Akkermansia muciniphila*.

The composition taught herein may be a pharmaceutical or supplement composition, e.g., in a form selected from the group consisting of capsule, tablet, and powder.

*E. hallii* and/or *I. butyriciproducens* and, optionally, propionate-producing bacterium, may be present in lyophilized or microencapsulated form.

*E. hallii* and/or *I. butyriciproducens* may be present in an amount ranging from about $10^4$ to about $10^{15}$ cells. Additionally, propionate-producing bacterium such as *A. muciniphila* may be present in an amount ranging from about $10^4$ to about $10^{15}$ cells.

The composition taught herein may further comprise a mucosal binding agent.

The composition taught herein may further comprise cobalt ions, for example, in the form of a cobalt salt such as cobalt chloride, cobalt sulphate, cobalt acetate, or cobalt nitrate.

The disclosure also pertains to the use of a composition comprising *E. hallii* and/or *I. butyriciproducens* and a physiologically acceptable carrier for increasing the production of pseudovitamin B12 in the intestine of a subject, and/or for increasing the production of propionate in the intestine of a subject.

The subject may suffer from vitamin B12 deficiency. The vitamin B12 deficiency in the subject may be derived from or caused by metformin treatment for type-2 diabetes, pernicious anemia, atrophic gastritis, chronic inflammation of the pancreas, surgical procedures where part of the stomach and/or small intestine are removed, weight loss surgery, inflammatory bowel disease (such as Crohn's disease, ulcerative colitis, and the like), celiac disease, bacterial growth, heavy drinking, Graves' disease, lupus, long-term use of acid-reducing drugs, malnutrition, bulimia and anorexia nervosa, HIV/AIDS, obesity, high body mass index, pre-diabetes state, insulin resistance, or a vegetarian or vegan diet.

The disclosure is further directed to *E. hallii* and/or *I. butyriciproducens* for use in treating and/or preventing vitamin B12 deficiency in a subject. The subject may suffer from vitamin B12 deficiency. The vitamin B12 deficiency in the subject may be derived from or caused by metformin treatment for type-2 diabetes, pernicious anemia, atrophic gastritis, chronic inflammation of the pancreas, surgical procedures where part of the stomach and/or small intestine are removed, weight loss surgery, inflammatory bowel disease (such as Crohn's disease, ulcerative colitis, and the like), celiac disease, bacterial growth, heavy drinking, Graves' disease, lupus, long-term use of acid-reducing drugs, malnutrition, bulimia, and anorexia nervosa, HIV/AIDS, obesity, high body mass index, pre-diabetes state, insulin resistance, or a vegetarian or vegan diet.

The disclosure further provides for *E. hallii* and/or *I. butyriciproducens* for increasing the production of pseudovitamin B12 in the intestine of a subject, and/or for increasing the production of propionate in the intestine of a subject. The subject may suffer from vitamin B12 deficiency. The vitamin B12 deficiency in the subject may be derived from or caused by metformin treatment for type-2 diabetes, pernicious anemia, atrophic gastritis, chronic inflammation of the pancreas, surgical procedures where part of the stomach and/or small intestine are removed, weight loss surgery, inflammatory bowel disease (such as Crohn's disease, ulcerative colitis, and the like), celiac disease, bacterial growth, heavy drinking, Graves' disease, lupus, long-term use of acid-reducing drugs, malnutrition, bulimia, and anorexia nervosa, HIV/AIDS, obesity, high body mass index, pre-diabetes state, insulin resistance, or a vegetarian or vegan diet.

Definitions

The term "syntrophic" or "syntrophy" as used herein, refers to the phenomenon that one species lives off the products of another species. In this association, the growth of one partner is improved or depends on the nutrients, growth factors or substrate provided by the other partner. This term for nutritional interdependence is often used in microbiology to describe this symbiotic relationship between some bacterial species.

The term "*Akkermansia muciniphila*" or "*A. muciniphila*" as used herein, refers to the anaerobic mucin-degrading bacteria first identified by Derrien (Derrien et al., 2004, *International Journal of Systematic and Evolutionary Microbiology* 54:1469-1476). Cells are oval-shaped, non-motile and stain Gram-negative. *A. muciniphila* may also be referred to as "*Akkermansia* spp." or "*Akkermansia*-like bacteria." *A. muciniphila* belongs to the Chlamydiae/Verrucomicrobia group; Verrucomicrobia phylum. If the taxonomy should change, the skilled artisan would know how to adapt the changes in the taxonomy to deduce the strains that could be used in the present disclosure. Moreover, the complete genome of *A. muciniphila* has been determined by van Passel et al., 2011, *PLoS One* 6:e16876. It is generally accepted that strains with a genome similarity of about 70% can be considered as the same species.

The term "mucolytic bacteria" or "gut mucosal-associated bacteria species" or "mucus-degrading bacteria" as used herein refers to bacteria that are associated with or are found in the vicinity of the gut mucosal barriers. "Gut mucosal-associated bacteria species" are further characterized in that they are able to degrade mucus. Non-limiting examples of "gut mucosal-associated bacteria species" include *A. muciniphila* (ATTC BAA-835), *Faecalibacterium prausnitzii* (A2-165), *Lactobacillus rhamnosus* (ATCC 53103) and *Bifidobacterium breve* (DSM-20213).

The term "corrinoids" as used herein refers to a class of chemically related compounds containing the biochemically rare element cobalt positioned in the center of a planar tetra-pyrrole ring called a corrin ring. Biosynthesis of the basic structure of the vitamin is accomplished only by bacteria and archaea (which usually produce the form hydroxocobalamin), but conversion between different forms of the vitamin can be accomplished in the human body.

The term "vitamin B12" or "B12 vitamers" generally refers to a class of chemically related compounds, all of which show biological activity. Vitamin B12 is often referred to as "cobalamin." The term "cobalamin" as used herein, generally refers to all forms of the vitamin B12. Specifically, cobalamins consist of a group of cobalt-containing vitamer compounds including cyanocobalamin, hydroxocobalamin (this form does occur in nature and is produced from bacterial hydroxocobalamin), and finally, the two naturally occurring co-factor forms of B12 in the human body, which include 5'-deoxyadenosylcobalamin and methylcobalamin.

The term "pseudovitamin B12" as used herein refers to Coα-[α-(7-adenyl)]-Coβ-cyanocobamide. This molecule differs from cobalamin in the α-ligand, where it has adenine instead of 5,6-dimethylbenzimidazole bound in an α-glycosidic linkage to C-1 of ribose.

The term "vitamin B12 deficiency," also known as "hypocobalaminemia," as used herein, refers to insufficient or low blood levels of vitamin B12, e.g., vitamin B12 levels below 120-180 picomole/L (170-250 pg/mL) in adults. Vitamin B12 deficiency in a subject typically derived from or occurred as a result of metformin treatment for type-2 diabetes, pernicious anemia, atrophic gastritis, chronic inflammation of the pancreas, surgical procedures where part of the stomach and/or small intestine are removed, weight loss surgery, Crohn's disease, celiac disease, bacterial growth, heavy drinking, Graves' disease, lupus, long-term use of acid-reducing drugs, malnutrition, bulimia and anorexia nervosa, HIV/AIDS, obesity, high body mass index, pre-diabetes state, insulin resistance, or a vegetarian or vegan diet and other conditions.

A subject suffering from vitamin B12 deficiency may show one or more symptoms such as diarrhea or constipation, fatigue, lack of energy, light-headedness when standing up, loss of appetite, pale skin, problems concentrating, shortness of breath (mostly during exercise), swollen red tongue or bleeding gums, low red blood cells, reduced heart function, nerve damage, confusion or change in mental status (e.g., dementia), irritability, depression, psychosis, loss of balance, poor muscle function, numbness and tingling of hands and feet, decreased taste, decreased fertility, and others. In young children, symptoms include poor growth, poor development, and difficulties with movement. Without early treatment some of the changes may be permanent.

The term "metformin" as used herein refers to a drug for the treatment of type 2 diabetes. The use of metformin has been associated with an increased incidence of vitamin B12 deficiency and reduced serum vitamin B12 levels in type 2 diabetes subjects treated with this drug. Metformin is believed to affect the gastrointestinal absorption system, and thus cause malabsorption of vitamin B12 in subjects treated with this drug.

The term "gut mucosal barrier" as taught herein, refers to natural mucosal barrier that acts as a selective barrier permitting the absorption of nutrients, electrolytes and water and preventing the exposure to detrimental macromolecules, micro-organisms, dietary and microbial antigens (e.g., food allergens). The gut mucosal barrier is essentially composed of a layer of mucus and an underlying layer of epithelial cells (referred to herein as "gut epithelial cells"). The gut epithelial cells are tightly linked to each other by so-called "tight junctions," which are basically "physical joints" between the membranes of two gut epithelial cells. Maintenance of the gut mucosal barrier, particularly maintenance of the physical integrity of the gut epithelial cell layer (i.e., keeping the junctions between cells tight), is crucial for protection of the host against the migration of pathogenic micro-organisms, antigens, and other undesirable agents from the intestine to the blood stream.

The gut mucosal barrier is also heavily colonized by approximately $10^{12}$-$10^{14}$ commensal microorganisms, mainly anaerobic or microaerophilic bacteria, most of which live in symbiosis with their host. These bacteria are beneficial to their host in many ways. They provide protection against pathogenic bacteria and serve a nutritional role in their host by synthesizing vitamin K and some of the components of the vitamin B complex. Further, the gut mucosal barrier has evolved a complex "gut mucosal immune system" for distinguishing between commensal (i.e., beneficial bacteria) and pathogenic bacteria and other detrimental agents. The gut mucosal immune system is an integral part of the gut mucosal barrier, and comprises lymphoid tissues and specialized immune cells (i.e., lymphocytes and plasma cells), which are scattered widely throughout the gut mucosal barrier. One of the microorganisms that naturally colonizes the mucosa of healthy subjects is the mucin-degrading *A. muciniphila*, which has been shown to increase the intestinal barrier function (Everard et al., *PNAS* 110 (2013) 9066-71; Reunanen et al., *Appl. Environ. Microbiol.* Mar. 20, 2015).

The term "probiotics" or "probiotic products" as used herein refers to microorganisms such as intestinal bacteria, which, when administered or ingested in effective amounts, confer health benefits to the host (e.g., humans or mammals). Preferably, probiotics should be alive or viable when administered to a subject so as to allow the probiotics to colonize the large intestine of the host. However, under certain conditions, probiotics may also be dead when administered provided that substances produced by the probiotics still exert probiotic, beneficial effects on the host. Most probiotics or probiotic products are composed of lactic acid bacteria such as *Lactobacilli* or Bifidobacteria. The skilled person is well-acquainted with the field of probiotics and knows how to select lactic acid bacteria endowed with probiotic activity.

The term "prebiotics" or "prebiotic products" as used herein generally refers to compounds that promote the growth and/or activity of GI microorganisms that contribute to the well-being of their host. Prebiotics or prebiotic products consist mainly of fermentable fibers or non-digestible carbohydrates. The fermentation of these fibers by probiotics promotes the production of beneficial end products, such as SCFAs, particularly butyrates. The skilled person is well-acquainted with the field of prebiotics and knows how to select ingredients endowed with prebiotic activity.

The term "symbiotics" or "symbiotic products" as used herein generally refers to compositions and/or nutritional supplements combining probiotics and one or more compounds that promote the growth and/or activity of GI microorganisms, such as prebiotics, into one product. The symbiotic beneficially affects the host by improving the survival and colonization of the probiotic in the GI tract, by selectively stimulating the growth and/or by activating the metabolism of the probiotic, thus improving host welfare. The skilled person is well-acquainted with symbiotics and knows how to select ingredients that may be combined into a symbiotic.

The term "beneficial intestinal bacteria species" as used herein refers to a bacterium species that inhabits (i.e., is innate) the mammalian (e.g., human) intestine and exerts beneficial effect(s) (e.g., protection against pathogenic bacteria species, production of butyric acid and/or butyrate and derivatives, etc.) on the GI, metabolic and other health of a mammal in which it resides.

Non-limiting examples of beneficial intestinal bacterial species include lactic acid bacteria from the genera *Lactobacillus* and *Bifidobacterium*. Other non-limiting examples of beneficial intestinal bacterial species include butyrate-producing bacterial species, which use the acetyl-CoA to produce butyric acid and/or butyrate and derivatives thereof, such as the bacterial strains disclosed in US 2014/0242654, WO 2014/150094 or WO 2013/032328 A1.

The term "effective amount" as used herein refers to an amount necessary to achieve an effect as taught herein. For instance, an effective amount of the intestinal bacterial strain or a strain derived therefrom as taught herein, i.e., *E. hallii* and/or *I. butyriciproducens*, and, optionally, *A. muciniphila*, is an amount that is effective in treating, preventing and or alleviating vitamin B12 deficiency in a subject. The effective amount can be readily determined without undue experimentation by a person of ordinary skill in the art. For instance, the skilled person can determine whether the amount of *E. hallii* and/or *I. butyriciproducens*, and, optionally, *A. muciniphila*, is effective in treating, preventing and/or alleviating vitamin B12 deficiency in a subject by measuring vitamin B12 levels in the blood and determine whether the vitamin B12 blood levels have returned to normal levels (approximately 137-546 picomole/L, as reviewed by Doets et al. 2013, *Ann. Nutr. Metab.* 62:311-322).

The term "physiologically acceptable carrier" or "alimentarily acceptable carrier," "nutritionally acceptable carrier" or "pharmaceutically acceptable carrier" as used herein refers to a physiologically acceptable or alimentarily acceptable carrier or nutritionally acceptable or pharmaceutically acceptable carrier material, such as a liquid or solid filler, diluent, excipient, solvent or encapsulating material, involved in providing an administration form of the polypeptide or host cell of the disclosure. Each carrier must be "acceptable" in the sense of being compatible with the other ingredients of the composition and not injurious to the subject, i.e., which are suitable for consumption or nutritionally acceptable. The term "suitable for consumption" or "nutritionally acceptable" refers to ingredients or substances that are generally regarded as safe for human (as well as other mammals) consumption. Non-limiting examples of materials, which can serve as physiologically acceptable carriers or nutritionally acceptable or pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminium hydroxide; (15) alginic acid; (16) pyrogen-free water; (17) isotonic saline; (18) Ringer's solution; (19) ethyl alcohol; (20) phosphate buffer solutions; (21) other non-toxic compatible substances employed in pharmaceutical formulations, and the like. Further, the terms "nutritionally acceptable" and "pharmaceutically acceptable" as used herein refer to those compositions or combinations of agents, materials, or compositions, and/or their dosage forms, which are within the scope of sound medical judgment, suitable for use in contact with the tissues of human beings and animals without excessive toxicity, irritation, allergic response, or other problem or complication, commensurate with a reasonable benefit/risk ratio.

The term "suitable for consumption" or "nutritionally acceptable" refers to ingredients or substances that are generally regarded as safe for human (as well as other mammals) consumption.

The term "about," as used herein indicates a range of normal tolerance in the art, for example, within two standard deviations of the mean. The term "about" can be understood as encompassing values that deviate at most 10%, 9%, 8%, 7%, 6%, 5%, 4%, 3%, 2%, 1%, 0.5%, 0.1%, 0.05%, or 0.01% of the indicated value.

The terms "comprising" or "to comprise" and their conjugations, as used herein, refer to a situation wherein the terms are used in their non-limiting sense to mean that items following the word are included, but items not specifically mentioned are not excluded. It also encompasses the more limiting verb "to consist essentially of" and "to consist of."

Reference to an element by the indefinite article "a" or "an" does not exclude the possibility that more than one of the elements is present, unless the context clearly requires that there be one and only one of the elements. The indefinite article "a" or "an" thus usually means "at least one."

The terms "to increase" and "increased level" and the terms "to decrease" and "decreased level" refer to the ability to significantly increase or significantly decrease or to a significantly increased level or significantly decreased level. Generally, a level is increased or decreased when it is at least 5%, such as 10%, 15%, 20%, 25%, 30%, 35%, 40%, 45%, 50% higher or lower, respectively, than the corresponding level in a control or reference. Alternatively, a level in a sample may be increased or decreased when it is statistically significantly increased or decreased compared to a level in a control or reference.

Surprisingly, it was found that a composition comprising *E. hallii* and/or *I. butyriciproducens* and an acceptable carrier could be used to treat, prevent and/or alleviate vitamin B12 deficiency in a subject administered with an effective amount of the composition. It was discovered that *E. hallii* and *I. butyriciproducens* has the ability to produce pseudovitamin B12.

Without being bound to any theories, it is believed that *E. hallii* and *I. butyriciproducens* produce and secrete pseudovitamin B12 in situ, i.e., in the intestine of a subject. Pseudovitamin B12 may then be immediately absorbed by the enterocytes of the host, where it may be directly used as a cofactor for vitamin B12-dependent enzymes or where it may be converted into a different form of vitamin B12 for use as a cofactor in vitamin B12-dependent enzymes.

It has been shown that pseudovitamin B12 can act as a cofactor for the three vitamin B12-dependent enzymes MetH, EutBC and PduCDE in *Salmonella enterica* (Anderson et al. 2008, *J. Bacteriol.* 190(4):1160-1171). It has been suggested that pseudovitamin B12 is the natural corrinoid produced by *Salmonella enterica* (Taga and Walker, 2008, *J. Bacteriol.* 190(4):1157-1159). Pseudovitamin B12 has been shown to be the dominant corrinoid produced by *Clostridium cohlearium, Lactobacillus reuteri, Nostoc commune, Aphanizomenon flos-aquae,* and *Aphanothece sacrum*. Moreover, it has been shown that pseudovitamin B12 produced by *Lactobacillus reuteri*, also an abundant mouse intestinal bacterium, can alleviate vitamin B12 deficiency in mice (Santos et al., 2007, *FEBS Letters* 581:4865-4870; Molina et al., 2009, *J. Appl. Microbiol.* 106:467-473).

In a first aspect, this disclosure relates to a composition comprising *E. hallii* and/or *I. butyriciproducens* and a physiologically acceptable carrier for use in treating and/or preventing vitamin B12 deficiency in a subject.

The physiologically acceptable carrier may be any inert carrier. For instance, non-limiting examples of suitable physiologically or pharmaceutically acceptable carriers include any of well-known physiological or pharmaceutical carriers, buffers, diluents, and excipients. It will be appreciated that the choice for a suitable physiological carrier will depend upon the intended mode of administration of the composition as taught herein (e.g., oral) and the intended form of the composition (e.g., beverage, yogurt, powder, capsules, and the like). The skilled person knows how to select a physiologically acceptable carrier, which is suitable for or compatible with the compositions for use as taught herein.

In an embodiment, the vitamin B12 deficiency in the subject is at least partially derived from or caused by metformin treatment for type-2 diabetes, pernicious anemia, atrophic gastritis, chronic inflammation of the pancreas, surgical procedures where part of the stomach and/or small intestine are removed, weight loss (bariatric) surgery, inflammatory bowel disease (such as Crohn's disease, ulcerative colitis, and the like), celiac disease, bacterial growth, heavy drinking, Graves' disease, lupus, long-term use of acid-reducing drugs, malnutrition, bulimia, and anorexia nervosa, HIV/AIDS, obesity, high body mass index, pre-diabetes state, insulin resistance, or a vegetarian or vegan diet.

In an embodiment, the composition for use as taught herein may further comprise propionate-producing and/or mucin-degrading bacteria, such as, without limitation, *A. muciniphila* or *Lactobacillus reuteri*. It was found that *E. hallii* and *A. muciniphila* have beneficial effect on each other. Without wishing to be bound by theory, it is thought that *A. muciniphila* provides a suitable substrate to *E. hallii*, while *E. hallii* provides. *muciniphila* with a source of vitami B12 to increase its growth and change its metabolite profile toward propionate production. It is expected that the same beneficial effect may be achieved between *E. hallii* and any other propionate-producing bacterium, or between *I. butyriciproducens* and any propionate-producing bacterium, including *A. muciniphila*. The propionate-producing and/or mucin-degrading bacteria may be administered simultaneously or sequentially to *E. hallii* and/or *I. butyriciproducens*.

In an embodiment, the composition for use as taught herein further comprises a cobalt compound, for example, in the form of a cobalt salt, such as cobalt chloride, cobalt sulphate, cobalt nitrate, cobalt acetate, and the like. The presence of supplemental cobalt may ensure production of sufficient corrin ring as a precursor for the pseudovitamin B12 produced by *E. hallii* and/or *I. butyriciproducens*. Alternatively, such cobalt compound may be administered to a subject suffering from or at risk of suffering from vitamin B12 deficiency and associated diseases and conditions taught herein in combination with the composition taught herein, in which case, the cobalt compound may be administered simultaneously or sequentially to the subject.

In an embodiment, the composition for use as taught herein may be in liquid form, e.g., a stabilized suspension of *E. hallii* and/or *I. butyriciproducens*, and, optionally, *A. muciniphila* as taught herein, or in solid form, e.g., a powder of lyophilized host cells as taught herein. In the case where *E. hallii* and/or *I. butyriciproducens*, and, optionally, *A. muciniphila*, are lyophilized, a cryoprotectant such as lactose, trehalose or glycogen may be employed. For oral administration, *E. hallii* and/or *I. butyriciproducens*, and, optionally, *A. muciniphila*, may be administered in solid dosage forms, such as capsules, tablets, and powders, or in liquid dosage forms, such as elixirs, syrups, and suspensions. *E. hallii* and/or *I. butyriciproducens*, and, optionally, *A. muciniphila*, may be encapsulated in capsules such as gelatin capsules, together with inactive ingredients and powder carriers, such as, e.g., glucose, lactose, sucrose, mannitol, starch, cellulose or cellulose derivatives, magnesium stearate, stearic acid, sodium saccharin, talcum, magnesium carbonate and the like.

Preferably, *E. hallii* and/or *I. butyriciproducens* is present in the composition taught herein in solid, lyophilized or dried form, for example, in powder or granular form. *E. hallii* and/or *I. butyriciproducens* may, for example, be present in the composition taught herein in microencapsulated form. The skilled person is capable of lyophilizing or microencapsulating *E. hallii* and/or *I. butyriciproducens* based on well-known techniques. Since *E. hallii* and/or *I.*

*butyriciproducens* is an obligate anaerobic bacterium, during lyophilization or microencapsulation oxygen-free conditions may be applied to preserve viability of *E. hallii* and/or *I. butyriciproducens*.

The technique of microencapsulation is well-known in the art for preserving probiotic bacteria (e.g., as reviewed by Serna-Cock and Vallejo-Castillo, 2013, *Afr. J. of Microbiol. Res.* 7(40):4743-4753, herein incorporated by reference). For example, any of the preservation techniques and preservation systems taught by Serna-Cock and Vallejo-Castillo may be employed in the present disclosure.

Lyophilization methods include, without limitation, slow, gradual freezing to −40° C. before drying, rapid freezing by placing at −80° C. before drying, or ultra rapid freezing by dripping cells with cryoprotector in liquid nitrogen before drying.

Cryoprotectants are often employed to protect probiotic compositions during lyophilization and to enhance shelf-life. Without limitation, a cryoprotectant selected from the group consisting of sucrose, maltose, maltodextrin, trehalose, mannitol, sorbitol, inulin, glycerol, DMSO, ethylene glycol, propylene glycol, 2-methyl-2,4-pentanediol, polyethylene glycol, polyvinylpyrrolidone, polyvinyl alcohol, polyglycerol, skim milk powder, milk protein, whey protein, UHT milk, betaine, adonitol, sucrose, glucose, lactose or any combination thereof, may be employed.

Prebiotics such as starch and wheat bran may further be added before lyophilization to enhance the efficacy of the *E. hallii* and/or *I. butyriciproducens* composition taught herein. Addition of antioxidants such as riboflavin, riboflavin phosphate or a physiologically acceptable salt thereof, glutathione, ascorbate, glutathione and cysteine to the lyophilization mixture may further enhance the viability of the *E. hallii* and/or *I. butyriciproducens* composition taught herein during storage, if required.

In an embodiment, the composition for use as taught herein may be a food or food supplement composition. Such food or food supplement composition may include a dairy product, more preferably a fermented dairy product, preferably a yogurt or a yogurt drink.

In an embodiment, the composition for use as taught herein may be a pharmaceutical composition, e.g., in a form selected from the group of capsule, tablet, and powder.

In an embodiment, *E. hallii* and/or *I. butyriciproducens* may be present in the composition as taught herein in an amount ranging from about $10^4$ to about $10^{15}$ cells, preferably colony forming units (CFU). For instance, an effective amount of the host cell may be an amount of about $10^5$ cells or CFU to about $10^{14}$ cells or CFU, preferably about $10^6$ cells or CFU to about $10^{13}$ cells or CFU, preferably about $10^7$ cells or CFU to about $10^{12}$ cells or CFU, more preferably about $10^8$ cells or CFU to about $10^{12}$ cells or CFU.

In an embodiment, *A. muciniphila*, if present, may be present in the composition as taught herein in an amount ranging from about $10^4$ to about $10^{15}$ cells, preferably colony forming units (CFU). For instance, an effective amount of the host cell may be an amount of about $10^5$ cells or CFU to about $10^{14}$ cells or CFU, preferably about $10^6$ cells or CFU to about $10^{13}$ cells or CFU, preferably about $10^7$ cells or CFU to about $10^{12}$ cells or CFU, more preferably about $10^8$ cells or CFU to about $10^{12}$ cells or CFU.

In an embodiment, the composition for use as taught herein may further comprise a mucosal binding agent.

The term "mucosal binding agent" or "mucosal binding polypeptide" as used herein refers to an agent or a polypeptide that is capable of attaching itself to the gut mucosal surfaces of the gut mucosal barrier of a mammal (e.g., human). A variety of mucosal binding polypeptides have been disclosed in the art. Non-limiting examples of mucosal binding polypeptide include bacterial toxin membrane binding subunits including, for example, the B subunit of cholera toxin, the B subunit of the *E. coli* heat-labile enterotoxin, *Bordetella pertussis* toxin subunits S2, S3, S4 and/or S5, the B fragment of Diphtheria toxin and the membrane binding subunits of Shiga toxin or Shiga-like toxins. Other suitable mucosal binding polypeptides include bacterial fimbriae proteins including, for example, *E. coli* fimbriae K88, K99, 987P, F41, FAIL, CFAIII ICES1, CS2 and/or CS3, CFAIIV ICS4, CS5 and/or CS6, P fimbriae, or the like. Other non-limiting examples of fimbriae include *Bordetella pertussis* filamentous hemagglutinin, *Vibrio cholerae* toxin-coregulate pilus (TCP), Mannose-sensitive hemagglutinin (MSHA), fucose-sensitive hemagglutinin (PSHA), and the like. Still other mucosal-binding agents include viral attachment proteins including influenza and sendai virus hemagglutinins and animal lectins or lectin-like molecules including immunoglobulin molecules or fragments thereof, calcium-dependent (C-type) lectins, selectins, collectins or helix pomatis hemagglutinin, plant lectins with mucosa-binding subunits including concanavalin A, wheat-germ agglutinin, phytohemagglutinin, abrin, ricin and the like.

In an embodiment, the compositions as taught herein may comprise one or more ingredient that is suitable for promoting survival and/or viability and/or maintaining the integrity of *E. hallii* and/or *I. butyriciproducens* and, optionally, *A. muciniphila*, during storage and/or during exposure to bile and/or during passage through the GI tract of a mammal (e.g., a human). Non-limiting examples of such ingredients include an enteric coating, and controlled release agents allowing passage through the stomach. The skilled person knows how to select suitable ingredients for ensuring that the active component (i.e., *E. hallii* and/or *I. butyriciproducens*, and, optionally, *A. muciniphila*) reaches its intended destination, where it exerts its action.

In an embodiment, the compositions for use as taught herein may further comprise ingredients selected from the group consisting of prebiotics, probiotics, carbohydrates, polypeptides, lipids, vitamins, minerals, medicinal agents, preservative agents, antibiotics, or any combination thereof.

In an embodiment, the compositions for use as taught herein may further comprise one or more ingredients, which further enhance the nutritional value and/or the therapeutic value of the compositions as taught herein. For instance, it may be advantageous to add one or more ingredients (e.g., nutritional ingredients, veterinary or medicinal agents, etc.) selected from proteins, amino acids, enzymes, mineral salts, vitamins (e.g., thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g., water-soluble and water-insoluble monosaccharides, disaccharides, and polysaccharides), medicinal compounds (e.g., antibiotics), antioxidants, trace element ingredients (e.g., compounds of cobalt, copper, manganese, iron, zinc, tin, nickel, chromium, molybdenum, iodine, chlorine, silicon, vanadium, selenium, calcium, magnesium, sodium and potassium and the like). The skilled person is familiar with methods and ingredients that are suitable to enhance the nutritional and/or therapeutic/medicinal value of the compositions as taught herein.

In a further aspect, the present disclosure relates to *E. hallii* and/or *I. butyriciproducens* for use in treating and/or preventing vitamin B12 deficiency in a subject.

In an embodiment, *E. hallii* and/or *I. butyriciproducens*, for the uses as taught herein, may be particularly indicated for a subject who suffers from vitamin B12 deficiency, where the vitamin B12 deficiency in the subject is caused by the conditions mentioned above.

Methods and Uses

In a further aspect, this disclosure relates to the use of a composition comprising *E. hallii* and/or *I. butyriciproducens* and a physiologically acceptable carrier for increasing the production of pseudovitamin B12 in the intestine of a subject.

In an embodiment, the composition comprising *E. hallii* and/or *I. butyriciproducens* and a physiologically acceptable carrier may be used in a method for increasing the production of pseudovitamin B12 in the intestine of a subject, the method comprising the step of administering an effective amount of the composition to the subject.

In an embodiment, the subject may be a subject that suffers from vitamin B12 deficiency, where the vitamin B12 deficiency in the subject is caused by the conditions mentioned above.

In a further aspect, the disclosure relates to the use of a composition comprising *E. hallii* and/or *I. butyriciproducens* and a physiologically acceptable carrier for increasing the production of propionate in the intestine of a subject.

In an embodiment, the composition comprising *E. hallii* and/or *I. butyriciproducens* and a physiologically acceptable carrier may be used in a method for increasing the production of propionate in the intestine of a subject, the method comprising the step of administering an effective amount of the composition to the subject.

In a further aspect, this disclosure relates to the use of *E. hallii* and/or *I. butyriciproducens* for increasing the production of pseudovitamin B12 in the intestine of a subject.

In an embodiment, *E. hallii* and/or *I. butyriciproducens* may be used in a method for increasing the production of pseudovitamin B12 in the intestine of a subject, the method comprising the step of administering an effective amount of the composition to the subject.

In an embodiment, *E. hallii* and/or *I. butyriciproducens* may be used in a method for increasing the production of pseudovitamin B12 in the intestine of a subject and may be particularly indicated for a subject suffering from vitamin B12 deficiency, where vitamin B12 deficiency derives from or is caused by any of the conditions as mentioned above.

In a further aspect, the present disclosure relates to the use of *E. hallii* and/or *I. butyriciproducens* for increasing the production of propionate in the intestine of a subject.

In an embodiment, *E. hallii* and/or *I. butyriciproducens* may be used in a method for increasing the production of propionate in the intestine of a subject, the method comprising the step of administering an effective amount of the composition to the subject.

In yet another aspect, this disclosure relates to an in vitro method for producing pseudovitamin B12, the method comprising the steps of culturing bacteria of the species *E. hallii* and/or *I. butyriciproducens* under conditions allowing production of pseudovitamin B12, and isolating the pseudovitamin B12 produced.

The skilled person is well aware of methods for isolating the pseudovitamin B12 produced.

The disclosure is further illustrated, but not limited, by the following examples. From the above discussion and these examples, one skilled in the art can ascertain the essential characteristics of this disclosure, and without departing from the teaching and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

BRIEF DESCRIPTION OF THE DRAWING

FIG. 1 shows measurement of *A. muciniphila* metabolites on mucus media with and without addition of vitamins or vitamin B12.

DETAILED DESCRIPTION

Example

Example 1: Bacterial Growth Conditions

*Akkermansia muciniphila*

*Akkermansia muciniphila* MucT (ATTC BAA-835) was grown as described previously (Derrien et al., 2004; Duncan et al., 2002). Incubations were performed in serum bottles sealed with butyl-rubber stoppers at 37° C. under anaerobic conditions provided by a gas phase of 182 kPa (1.5 atm) $N2/CO2(80/20$ ratio). Growth was measured by spectrophotometer as optical density at 600 nm (OD600).

*E. hallii*

*Eubacterium hallii* L2-7 was grown anaerobically at 37° C. in YCFA with some adjustments. Mucin sugar utilization was performed in minimal media with or without an addition of 10 mM acetate. In the case where the experiments were performed with mucin-derived single sugars (mannose, fucose, galactose, N-acetyl galactosamine, or N-acetyl glucosamine), these were used at a concentration of 25 mM. The growth was followed for 24 hours and samples were collected regularly for OD600 and HPLC analysis.

Co-Culture Experiments

Co-culture experiments were performed in minimal media supplemented with mucus (Derrien et al., 2004). Optimal co-culture conditions were established as follows. *A. muciniphila* was added to mucin media followed by 8 hours of incubation to reach measurable concentrations of acetate and liberate sugars. Subsequently, cells of *E. hallii* were added to the *A. muciniphila*-containing incubations. All cells had been washed twice with PBS before addition to the co-culture to prevent overflow of products from the pre-culture. During the co-culture, 0.15% mucin was added to the media every 48 hours to maintain sufficient substrate availability for *A. muciniphila*.

Analysis of the Fermentation Products Produced by the Bacterial Co-Culture

High-performance liquid chromatography (HPLC) was used for analysis of fermentation products from the co-culture described above. For the fermentation product analysis, 1 ml of bacterial culture was centrifuged and the supernatant was stored at −20° C. until the HPLC analysis. Substrate conversion and product formation were measured with a Thermo Scientific Spectra system high-performance liquid chromatography (HPLC) system equipped with a Varian Metacarb 67H 300×6.5 mm column kept at 45° C. and running with 0.005 mM sulfuric acid as eluent. The eluent had a flow of 0.8 ml/minute and metabolites were detected by determining the refractive index.

Vitamin B12 Analysis

Ultra-high performance liquid chromatography mass spectrometry (UHPLC-MS) was used for vitamin B12 analysis. Briefly, *E. hallii* cells (0.2 g) were mixed with 10 mL of extraction buffer (8.3 mM sodium hydroxide and 20.7 mM acetic acid, pH 4.5) containing 100 μL of 1% NaCN. The vitamin was extracted in its cyano-form by subjecting the mixture to a boiling water bath for 30 minutes. After cooling, the extract was recovered by centrifugation (6900 g for 10 minutes; Hermle, Wehingen, Germany) and finally purified by immunoaffinity column chromatography (Easy-Extract; R-Biopharma, Glasgow, Scotland). The reconstituted extract was analyzed for the vitamin content using a HSS T3 C18 column (2.1×100 mm; 1.8 μm) on a Waters Acquity UPLC system (Milford, Mass., USA) equipped with a photodiode array detector (PDA; 210-600 nm) and interfaced to a high resolution quadrupole time-of-flight mass spectrometer (QTOF; Synapt G2-Si, Waters). The eluent was a gradient flow (0.32 ml/minute) of water (solvent A) and acetonitrile (solvent B), both acidified with 0.1% formic acid: 0-0.5 minute (95:5); 0.5-5 minutes (60:40); 5-6 minutes (60:40) and 6-10 minutes (95:5). The column 22 was maintained at 30° C. and the UV detection was recorded at 361 nm. The MS analysis was done in positive ion mode with electrospray ionization, using a scanning range set for m/z of 50-1500. The parent ions corresponding to the vitamin peak were further fragmented (MS/MS) and analyzed.

Results

Vitamin B12-Dependent Syntrophy Between *E. hallii* and *A. muciniphila*

In the co-culture of *A. muciniphila* with *E. hallii*, the proportion of succinate to propionate had shifted compared to monocultures of *A. muciniphila*. Production of propionate by methylmalonyl-CoA synthase is known to depend on the co-factor vitamin B12. Therefore, the effect of vitamins and vitamin B12 was tested on monocultures of *A. muciniphila*. Addition of a vitamin mixture or only vitamin B12 indeed switched the succinate to propionate profile of *A. muciniphila* in the same way the presence of *E. hallii* did in the co-culture (FIG. 1). Detailed analysis by mass spectroscopy showed that *E. hallii* is capable of synthesizing a B12 vitamer in monocultures. The structure of the vitamer appeared to be pseudovitamin B12 as the lower ligand contained adenine instead of 5,6-dimethylbenzimidazole (DMB). No effect of DMB addition was observed on the structure of the produced B12 vitamer (data not shown). Taken together, this is evidence for a bidirectional metabolic cross-feeding between *A. muciniphila* and *E. hallii*, where *A. muciniphila* provides sugars for growth support of *E. hallii* that in return provides *A. muciniphila* with sufficient levels of a vitamin B12 analogue used as a co-factor for the conversion of succinate to propionate via methylmalonyl-CoA synthase. Both vitamin B12 and pseudovitamin B12 can be used as a cofactor by *A. muciniphila* and activate the methylmalonyl-CoA synthase. Hence, this syntrophic relationship appears to be co-evolved within the intestinal tract as the B12 vitamer produced by *E. hallii* is pseudovitamin B12 form.

In the case of *E. hallii*, a specific metabolic and co-factor syntrophic interaction was observed, as it produced pseudovitamin B12 that affected the carbon flux within *A. muciniphila*, resulting in propionate production. It is known from human studies that propionate delivered to the colon has various beneficial effects, including the reduction of appetite (Chambers et al., 2015, supra).

The fact that a changed metabolic profile for *A. muciniphila* in the presence of *E. hallii* was found further testifies for a mutualistic syntrophic interaction. The syntrophic partners together produce a higher propionate to succinate ratio, which is beneficial for host cell metabolism. In addition, a B12 cofactor is produced, which may be used by the host to prevent and/or treat vitamin B12 deficiency.

Many gastrointestinal disorders have been associated with mucosal damage and lower gut barrier function. The fact that intestinal bacteria may have an impact on both these factors, either directly or via specific immune and metabolic stimulation, further emphasizes the importance of having the right bacteria at the right place. Loss of mucosal integrity and the associated mucobiome could be indicative for disease states and its development. *A. muciniphila* has been positively associated with a lean phenotype and beneficial metabolic gene regulation in human cell types (Everard et al., 2013; Lukovac et al., 2015). Its presence might be essential for a mucosal adherent network of beneficial microorganisms that together prompt these effects of the host. As a matter of fact, weight loss studies usually report increased abundance of Verrucomicrobia (mainly *A. muciniphila*) as well as several other microbial species (Liou et al., 2013; Remely et al., 2015; Ward et al., 2014). Taken together, these results further indicate the possible importance of mucosal-associated microbial networks and their metabolic cross-feeding for regulation of host health-related parameters and prevention of disease.

Example 2: Vitamin B12 Production by *Intestinimonas butyriciproducens*

*Intestinimonas butyriciproducens* AF211 was grown as described on glucose-acetate medium (Bui et al., 2015, Nature Comm. 6:10062). Further detailed analysis by mass spectroscopy showed that *I. butyriciproducens* AF 211 is capable of synthesizing a B12 vitamer in monocultures. The structure of the vitamer was the same as that produced by *E. hallii* and was identified as pseudovitamin B12 as the lower ligand contained adenine instead of 5,6-dimethylbenzimidazole (DMBI). No effect of DMB addition was observed on the structure of the produced B12 vitamer (data not shown).

The invention claimed is:

1. A method of treating vitamin B12 deficiency in a subject, the method comprising:

administering a composition comprising:

an amount of *Eubacterium hallii* and/or *Intestinimonas butyriciproducens* effective to increase production of pseudovitamin B12 and/or propionate in the subject's intestine, and a physiologically acceptable carrier to the subject so as to treat vitamin B12 deficiency in the subject.

2. The method according to claim 1, wherein the subject has been diagnosed as having a vitamin B12 deficiency, and the vitamin B12 deficiency is secondary to a condition selected from the group consisting of metformin treatment for type-2 diabetes, pernicious anemia, atrophic gastritis, chronic inflammation of the pancreas, a surgical procedure where part of the stomach and/or small intestine are removed, weight loss (bariatric) surgery, inflammatory bowel disease, Crohn's disease, ulcerative colitis, celiac disease, bacterial infection, heavy drinking, Graves' disease, lupus, long-term use of acid-reducing drugs, malnutrition, bulimia, anorexia nervosa, HIV/AIDS, obesity, high body mass index, pre-diabetes state, insulin resistance, a vegetarian diet, a vegan diet, and any combination thereof.

3. The method according to claim 1, wherein the composition further comprises:
a propionate-producing bacterium.

4. The method according to claim 3, wherein the propionate-producing bacterium is present in the composition in an amount ranging from about $10^4$ to about $10^{15}$ cells.

5. The method according to claim 3, wherein the propionate-producing bacterium is *Akkermansia muciniphila*.

6. The method according to claim 1, wherein the composition is a pharmaceutical or supplement composition in a form selected from the group consisting of a capsule, tablet, and powder.

7. The method according to claim 1, wherein the *I. butyriciproducens* and/or *E. hallii* and, optionally, a propionate-producing bacterium, is present in lyophilized or microencapsulated form in the composition.

8. The method according to claim 1, wherein *I. butyriciproducens* and/or *E. hallii* is present in the composition in an amount ranging from about $10^4$ to about $10^{15}$ cells.

9. The method according to claim 1, wherein the composition further comprises:
a mucosal binding agent.

10. The method according to claim 1, wherein the composition further comprises:
a cobalt source selected from the group consisting of cobalt ions, a cobalt salt, cobalt chloride, cobalt sulphate, cobalt acetate, cobalt nitrate, and any combination thereof.

11. The method according to claim 1, wherein the method treats vitamin B12 deficiency in a subject.

12. A method of treating a subject to increase production of pseudovitamin B12 and/or propionate in the subject's intestine, the method comprising:
administering a composition comprising:
an amount of *Intestinimonas butyriciproducens* and/or *Eubacterium hallii* effective to increase production of pseudovitamin B12 and/or propionate in the subject's intestine, and
a physiologically acceptable carrier
to the subject so as to increase the production of pseudovitamin B12 and/or propionate in the subject's intestine so as to treat the subject.

13. The method according to claim 12, wherein the subject has been diagnosed as having a vitamin B12 deficiency.

14. The method according to claim 13, wherein the subject has a vitamin B12 deficiency secondary to a condition selected from the group consisting of metformin treatment for type-2 diabetes, pernicious anemia, atrophic gastritis, chronic inflammation of the pancreas, a surgical procedure where part of the stomach and/or small intestine are removed, weight loss surgery, inflammatory bowel disease, Crohn's disease, ulcerative colitis, celiac disease, bacterial infection, heavy drinking, Graves' disease, lupus, long-term use of acid-reducing drugs, malnutrition, bulimia, anorexia nervosa, HIV/AIDS, obesity, high body mass index, pre-diabetes state, insulin resistance, a vegetarian diet, a vegan diet, and any combination thereof.

15. The method according to claim 12, wherein the composition consists of *I. butyriciproducens* and a physiologically acceptable carrier.

16. A method of treating vitamin B12 deficiency in a subject, the method comprising:
administering to the subject an amount of *Eubacterium hallii* and/or *Intestinimonas butyriciproducens* effective to produce pseudovitamin B12 and/or propionate in the subject's intestine, so as to treat and/or prevent vitamin B12 deficiency in the subject.

17. The method according to claim 16, wherein the subject has a vitamin B12 deficiency secondary to a condition selected from the group consisting of metformin treatment for type-2 diabetes, pernicious anemia, atrophic gastritis, chronic inflammation of the pancreas, a surgical procedure where part of the stomach and/or small intestine are removed, weight loss surgery, inflammatory bowel disease, Crohn's disease, ulcerative colitis, celiac disease, bacterial infection, heavy drinking, Graves' disease, lupus, long-term use of acid-reducing drugs, malnutrition, bulimia, anorexia nervosa, HIV/AID S, obesity, high body mass index, pre-diabetes state, insulin resistance, a vegetarian diet, a vegan diet, and any combination thereof.

18. The method according to claim 16, wherein the method treats vitamin B12 deficiency in a subject.

19. A method of treating a subject diagnosed as having a vitamin B12 deficiency to increase production of pseudovitamin B12 and/or propionate in the subject's intestine, the method comprising:
administering to the subject an amount of a composition comprising *Eubacterium hallii* and/or *Intestinimonas butyriciproducens* effective to increase the production of pseudovitamin B12 and/or propionate in the subject's intestine,
so as to treat the subject's vitamin B12 deficiency thereby.

20. The method according to claim 19, wherein the composition consists of *I. butyriciproducens* and a physiologically acceptable carrier.

21. The method according to claim 19, wherein the subject has a vitamin B12 deficiency secondary to a condition selected from the group consisting of metformin treatment for type-2 diabetes, pernicious anemia, atrophic gastritis, chronic inflammation of the pancreas, surgical procedure where part of the stomach and/or small intestine are removed, weight loss surgery, inflammatory bowel disease, Crohn's disease, ulcerative colitis, celiac disease, bacterial growth, heavy drinking, Graves' disease, lupus, long-term use of acid-reducing drugs, malnutrition, bulimia, anorexia nervosa, HIV/AIDS, obesity, high body mass index, pre-diabetes state, insulin resistance, a vegetarian diet, a vegan diet, and any combination thereof.

* * * * *